United States Patent
Soito et al.

(10) Patent No.: US 7,989,207 B2
(45) Date of Patent: Aug. 2, 2011

(54) TESTING LUMENECTOMY SAMPLES FOR MARKERS OF NON-VASCULAR DISEASES

(75) Inventors: Angela Soito, Oakland, CA (US); John B. Simpson, Woodside, CA (US)

(73) Assignee: Tyco Healthcare Group LP, Mansfield, MA (US)

(*) Notice: Subject to any disclaimer, the term of this patent is extended or adjusted under 35 U.S.C. 154(b) by 659 days.

(21) Appl. No.: 11/356,460

(22) Filed: Feb. 17, 2006

(65) Prior Publication Data

US 2007/0196926 A1 Aug. 23, 2007

(51) Int. Cl.
*G01N 33/48* (2006.01)
*G01N 1/04* (2006.01)

(52) U.S. Cl. ............... 436/63; 436/71; 436/86; 436/174; 600/564

(58) Field of Classification Search .................... 436/63, 436/71, 86, 174; 600/564
See application file for complete search history.

(56) References Cited

U.S. PATENT DOCUMENTS

| | | | |
|---|---|---|---|
| 2,178,700 A | 11/1939 | Henry | |
| 3,705,577 A | 12/1972 | Sierra | |
| 3,815,604 A | 6/1974 | O'Malley et al. | |
| 3,837,345 A | 9/1974 | Matar | |
| 3,995,619 A | 12/1976 | Glatzer | |
| 4,210,146 A | 7/1980 | Banko | |
| 4,669,469 A | 6/1987 | Gifford et al. | |
| 4,696,298 A | 9/1987 | Higgins et al. | |
| 4,771,774 A | 9/1988 | Simpson et al. | |
| 4,781,186 A | 11/1988 | Simpson et al. | |
| 4,817,613 A | 4/1989 | Jaraczewski et al. | |
| 4,819,635 A | 4/1989 | Shapiro | |
| 4,850,957 A | 7/1989 | Summers | |
| 4,926,858 A | 5/1990 | Gifford, III et al. | |
| RE33,258 E | 7/1990 | Onik et al. | |
| 4,966,604 A | 10/1990 | Reiss | |
| 4,979,951 A | 12/1990 | Simpson | |
| 4,986,807 A | 1/1991 | Farr | |
| 4,994,067 A | 2/1991 | Summers | |
| 5,024,651 A | 6/1991 | Shiber | |
| 5,047,040 A | 9/1991 | Simpson et al. | |
| 5,053,044 A | 10/1991 | Mueller et al. | |
| 5,071,425 A | 12/1991 | Gifford et al. | |
| 5,084,010 A | 1/1992 | Plaia et al. | |
| 5,087,265 A | 2/1992 | Summers | |
| 5,092,873 A | 3/1992 | Simpson et al. | |
| 5,154,724 A | 10/1992 | Andrews | |
| 5,181,920 A | 1/1993 | Mueller et al. | |
| 5,217,474 A | 6/1993 | Zacca et al. | |
| 5,222,966 A | 6/1993 | Perkins et al. | |
| 5,224,488 A | 7/1993 | Neuffer | |
| 5,224,949 A | 7/1993 | Gomringer et al. | |
| 5,226,909 A | 7/1993 | Evans et al. | |
| 5,226,910 A | 7/1993 | Kajiyama et al. | |
| 5,242,460 A | 9/1993 | Klein et al. | |
| 5,250,059 A | 10/1993 | Andreas et al. | |
| 5,250,065 A | 10/1993 | Clement et al. | |
| 5,269,793 A | 12/1993 | Simpson et al. | |
| 5,282,484 A | 2/1994 | Reger | |
| 5,285,795 A | 2/1994 | Ryan et al. | |
| 5,312,425 A | 5/1994 | Evans et al. | |
| 5,318,032 A | 6/1994 | Lonsbury et al. | |
| 5,318,528 A | 6/1994 | Heaven et al. | |
| 5,321,501 A | 6/1994 | Swanson et al. | |
| 5,372,602 A | 12/1994 | Burke | |
| 5,395,313 A | 3/1995 | Naves et al. | |
| 5,403,334 A | 4/1995 | Evans et al. | |
| 5,419,774 A | 5/1995 | Willard et al. | |
| 5,429,136 A | 7/1995 | Milo et al. | |
| 5,431,673 A | 7/1995 | Summers et al. | |
| 5,441,510 A | 8/1995 | Simpson et al. | |
| 5,459,570 A | 10/1995 | Swanson et al. | |
| 5,470,415 A | 11/1995 | Perkins et al. | |
| 5,485,042 A | 1/1996 | Burke | |
| 5,491,524 A | 2/1996 | Hellmuth et al. | |
| 5,505,210 A | 4/1996 | Clement | |
| 5,507,292 A | 4/1996 | Jang et al. | |
| 5,507,760 A | 4/1996 | Wynne et al. | |
| 5,507,795 A | 4/1996 | Chiang et al. | |
| 5,514,115 A | 5/1996 | Frantzen et al. | |
| 5,527,325 A | 6/1996 | Conley et al. | |
| 5,549,601 A | 8/1996 | McIntyre et al. | |
| 5,569,277 A | 10/1996 | Evans et al. | |
| 5,571,122 A | 11/1996 | Kelly et al. | |

(Continued)

FOREIGN PATENT DOCUMENTS

EP 0 999 447 A1 5/2000

(Continued)

OTHER PUBLICATIONS

Sobel et al. Circulation, vol. 97, 1998, pp. 2213-2221.*
Virdis et al. "Spirolactone improves angiotensin-induced vascular changes and oxidtative stress," *Hypertension*, vol. 40, Oct. 2002, pp. 504-510.
Forero McGrath M. et al. "The endocrine function of the heart," *Trends Endocrinol. Metabol.*, vol. 16, No. 10, Dec. 2005, pp. 469-477.
U.S. Appl. No. 11/010,833, filed Dec. 13, 2004, Simpson.
Ballantyne, et al., "Markers of Inflammation and Their Clinical Significance", *Athera Supp.* 6:21-29 (2005).

(Continued)

*Primary Examiner* — Maureen M Wallenhorst
(74) *Attorney, Agent, or Firm* — Alana T. Bergman, Esq.

(57) ABSTRACT

Lumenectomy material is tested to determine the presence or likelihood of a condition of a patient. The lumenectomy material is in the form of at least one continuous tissue strand collected in vivo from an inner surface of a body lumen of the patient. The presence of at least one marker of a disease is determined. The disease may be hypertension, hyperlipidemia, depression, obesity, metabolic syndrome, insulin resistance, kidney damage, or diabetes. The patient is identified as having or as likely to develop the disease if a marker of the disease is identified in the lumenectomy material of the patient.

25 Claims, No Drawings

U.S. PATENT DOCUMENTS

| | | | |
|---|---|---|---|
| 5,571,130 A * | 11/1996 | Simpson et al. | 606/171 |
| 5,584,842 A | 12/1996 | Fogarty et al. | |
| 5,620,447 A | 4/1997 | Smith et al. | |
| 5,624,457 A | 4/1997 | Farley et al. | |
| 5,632,754 A | 5/1997 | Farley et al. | |
| 5,634,464 A | 6/1997 | Jang et al. | |
| 5,643,296 A | 7/1997 | Hundertmark et al. | |
| 5,643,298 A | 7/1997 | Nordgren et al. | |
| 5,665,098 A | 9/1997 | Kelly et al. | |
| 5,669,920 A | 9/1997 | Conley et al. | |
| 5,674,232 A | 10/1997 | Halliburton | |
| 5,695,506 A | 12/1997 | Pike et al. | |
| 5,700,687 A | 12/1997 | Finn | |
| 5,709,698 A | 1/1998 | Adams et al. | |
| 5,731,489 A * | 3/1998 | Ganten et al. | 800/9 |
| 5,733,296 A | 3/1998 | Rogers et al. | |
| 5,741,270 A | 4/1998 | Hansen et al. | |
| 5,776,114 A | 7/1998 | Frantzen et al. | |
| 5,816,923 A | 10/1998 | Milo et al. | |
| 5,836,957 A | 11/1998 | Schulz et al. | |
| 5,843,103 A | 12/1998 | Wulfman | |
| 5,868,685 A | 2/1999 | Powell et al. | |
| 5,868,767 A | 2/1999 | Farley et al. | |
| 5,911,734 A | 6/1999 | Tsugita et al. | |
| 5,916,210 A | 6/1999 | Winston | |
| 5,938,671 A | 8/1999 | Katoh et al. | |
| 5,948,184 A | 9/1999 | Frantzen et al. | |
| 5,951,482 A | 9/1999 | Winston et al. | |
| 5,954,745 A | 9/1999 | Gertler et al. | |
| 5,968,064 A | 10/1999 | Selmon et al. | |
| 5,989,281 A | 11/1999 | Barbut et al. | |
| 6,010,449 A | 1/2000 | Selmon et al. | |
| 6,013,072 A | 1/2000 | Winston et al. | |
| 6,022,362 A | 2/2000 | Lee et al. | |
| 6,027,450 A | 2/2000 | Brown et al. | |
| 6,027,514 A | 2/2000 | Stine et al. | |
| 6,036,656 A | 3/2000 | Slater | |
| 6,036,707 A | 3/2000 | Spaulding | |
| 6,048,349 A | 4/2000 | Winston et al. | |
| 6,063,093 A | 5/2000 | Winston et al. | |
| 6,068,638 A | 5/2000 | Makower | |
| 6,081,738 A | 6/2000 | Hinohara et al. | |
| 6,106,515 A | 8/2000 | Winston et al. | |
| 6,120,515 A | 9/2000 | Rogers et al. | |
| 6,120,516 A | 9/2000 | Selmon et al. | |
| 6,126,649 A | 10/2000 | VanTassel et al. | |
| 6,134,003 A | 10/2000 | Tearney et al. | |
| 6,157,852 A | 12/2000 | Selmon et al. | |
| 6,159,225 A | 12/2000 | Makower | |
| 6,183,432 B1 | 2/2001 | Milo | |
| 6,190,353 B1 | 2/2001 | Makower et al. | |
| 6,191,862 B1 | 2/2001 | Swanson et al. | |
| 6,193,676 B1 | 2/2001 | Winston et al. | |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,228,076 B1 | 5/2001 | Winston et al. | |
| 6,231,546 B1 | 5/2001 | Milo et al. | |
| 6,231,549 B1 | 5/2001 | Noecker et al. | |
| 6,235,000 B1 | 5/2001 | Milo et al. | |
| 6,241,667 B1 * | 6/2001 | Vetter et al. | |
| 6,241,744 B1 * | 6/2001 | Imran et al. | |
| 6,258,052 B1 * | 7/2001 | Milo | |
| 6,266,550 B1 * | 7/2001 | Selmon et al. | |
| 6,283,951 B1 * | 9/2001 | Flaherty et al. | |
| 6,283,983 B1 * | 9/2001 | Makower et al. | |
| 6,299,622 B1 * | 10/2001 | Snow et al. | |
| 6,302,875 B1 * | 10/2001 | Makower et al. | |
| 6,330,884 B1 * | 12/2001 | Kim | |
| 6,355,005 B1 * | 3/2002 | Powell et al. | |
| 6,375,615 B1 * | 4/2002 | Flaherty et al. | |
| 6,394,976 B1 * | 5/2002 | Winston et al. | |
| 6,398,798 B2 * | 6/2002 | Selmon et al. | |
| 6,428,552 B1 * | 8/2002 | Sparks | |
| 6,443,966 B1 * | 9/2002 | Shiu | |
| 6,445,939 B1 * | 9/2002 | Swanson et al. | |
| 6,447,525 B2 * | 9/2002 | Follmer et al. | |
| 6,623,496 B2 * | 9/2003 | Snow et al. | |
| 6,638,233 B2 * | 10/2003 | Corvi et al. | |
| 2002/0022788 A1 * | 2/2002 | Corvi et al. | |
| 2002/0077642 A1 * | 6/2002 | Patel et al. | |
| 2003/0018346 A1 * | 1/2003 | Follmer et al. | |
| 2003/0100486 A1 * | 5/2003 | Ridker et al. | 514/3 |
| 2003/0120295 A1 * | 6/2003 | Simpson et al. | |
| 2003/0125757 A1 * | 7/2003 | Patel et al. | |
| 2003/0125758 A1 * | 7/2003 | Simpson et al. | |
| 2003/0219813 A1 * | 11/2003 | Yang et al. | 435/6 |
| 2004/0167553 A1 | 8/2004 | Simpson | |
| 2004/0167554 A1 | 8/2004 | Simpson | |
| 2005/0154407 A1 * | 7/2005 | Simpson | 606/159 |
| 2005/0177050 A1 | 8/2005 | Cohen | |
| 2005/0177068 A1 * | 8/2005 | Simpson | 600/564 |
| 2005/0222519 A1 * | 10/2005 | Simpson | |
| 2005/0222663 A1 * | 10/2005 | Simpson et al. | |
| 2006/0032508 A1 * | 2/2006 | Simpson | 128/898 |
| 2006/0235366 A1 * | 10/2006 | Simpson | 604/508 |
| 2006/0236019 A1 * | 10/2006 | Soito et al. | 711/1 |
| 2006/0239982 A1 * | 10/2006 | Simpson | |
| 2007/0078469 A1 * | 4/2007 | Soito et al. | |
| 2007/0173901 A1 * | 7/2007 | Reeve | 607/45 |
| 2007/0218519 A1 * | 9/2007 | Urdea et al. | 435/7.92 |
| 2008/0065124 A1 * | 3/2008 | Olson | |
| 2008/0065125 A1 * | 3/2008 | Olson | |

FOREIGN PATENT DOCUMENTS

| | | |
|---|---|---|
| WO | WO 00/18903 | 4/2000 |
| WO | WO 02/19966 A2 | 3/2002 |
| WO | WO 02/45598 A2 * | 6/2002 |
| WO | WO 03/016910 A1 | 2/2003 |
| WO | WO 2004/089184 A2 | 10/2004 |

OTHER PUBLICATIONS

Ballantyne, et al., "Lipoprotein-Associated Phospholipase $A_2$, High-Sensitivity C-Reactive Protein, and Risk for Incident Coronary Heart Disease in Middle-Aged Men and Women in the Atherosclerosis Risk in Communities (ARIC) Study", *Circulation* 109:837-842 (2004).

Brilakis, et al., "Association of lipoprotein-associated phospholipase A2 levels with coronary artery disease risk factors, angiographic coronary artery disease, and major adverse events at follow-up", *European Heart Journal* 26(2):137-144 (2005).

Cipollone, et al., "High preprocedural non-HDL cholesterol is associated with enhanced oxidative stress and monocyte activation after coronary angioplasty: possible implications in restenosis" *Heart* 89:773-779 (2003).

Hojo, et al., "Matrix metalloproteinase expression in the coronary circulation induced by coronary angioplasty" *Atherosclerosis* 161:185-193 (2002).

Hojo, et al., "Chemokine expression in coronary circulation after coronary angioplasty as a prognostic factor for restenosis" *Atherosclerosis* 156:165.170 (2001).

Hojo, et al., "Interleukin 6 expression in coronary circulation after coronary angioplasty as a risk factor for Restenosis" *Heart* 84:83-87 (2000).

Horie, et al., "Association of an Acute Reduction in Lipoprotein(a) With Coronary Artery Restenosis After Percutaneous Transluminal Coronary Angioplasty" *Circulation* 96(1):166-173 (1997).

Inoue, et al., "Expression of Polymorphonuclear Leukocyte Adhesion Molecules and Its Clinical Significance in Patients Treated with Percutaneous Transluminal Coronary Angioplasty" *JACC* 28(5):1127-1133 (1996).

Kurz, et al., "Increased serum concentrations of adhesion molecules after coronary angioplasty" *Clinical Science* 87:627-633 (1994).

Mukherjee, et al., "Elective coronary revascularization, an iatrogenic form of acute coronary syndrome: How can clinicians reduce the risk?", *American Heart Journal* 148(3):371-377 (2004).

Tashiro, et al., "Role of cytokines in the pathogenesis of restenosis after percutaneous transluminal coronary angioplasty" *Coronary Artery Disease* 12(2):107-113 (2001).

Winkler, et al., "Platelet-Activating Factor Acetylhydrolase Activity Indicates Angiographic Coronary Artery Disease Independently of Systemic Inflammation and Other Risk Factors" *Circulation* 111:980-987.

Yoffe et al., "Preliminary Experience with the Xtrak Debulking Device in the Treatment of Peripheral Occulasions", Journal of Endovascular Therapy, vol. 9, No. 2, pp. 234-240.

"MollRing Cutter", Vascular Architects, www.vasculararchitects.com/pages/products_MollRing_Intl.html, Sep. 28, 2004.

Takagi et al., "Effective Plaque Removal With a New 8 French-Compatible Atherectomy Catheter", Catheter Cardiovasc Interv., Aug. 2002, vol. 56, No. 5, pp. 452-459.

"FLEXI-CUT® Directional Debulking System: Indications, Contraindications, Warnings, Precautions, Adverse Effects", www.guidant.com/products/ProductTemplates/VI/dca_ifu.shtml, Sep. 29, 2004.

Rosenthal et al., "Remote Superficial Femoral Artery Endarterectomy and Distal aSpite Stenting: Multicenter Medium-Term Results", Journal of Vascular Surgery, Jul. 2004, vol. 40, No. 1, pp. 67-72.

Ahn et al., "Status of Peripheral Atherectomy", Endovascular Surgery, Surgical Clinics of North America, vol. 72, No. 4, Aug. 1992, pp. 869-878.

Kuffer et al., "Simpson's Atherectomy of the Peripheral Arteries: Early Results and Follow-up", Rofo Fortschr Geb Rontgnestr Neuen Blidgeb Verfahr, Jul. 1990, vol. 153, No. 1, pp. 61-67.

Kuffer, "Peripheral Simpson Atherectomy, Indications and Results of a New Transluminal Procedure for Vascular Recanalization", Radiologe, Feb. 1990, vol. 30, No. 2, pp. 60-65.

Kuffer et al., "Secondary Simpson Atherectomy of Femoro-Popliteal Obstructions. Alternative or Supplementary Procedure to the Femoral Stent?", Vasa Suppl., 1992, vol. 35, p. 187.

Kuffer et al., "Simpson's Atherectomy in Embolizing Leg Artery Stenoses", Rofo Fortschr Geb Rontgenstr Neuen Blldgeb Verfahr, Sep. 1991, vol. 155, No. 3, pp. 235-241.

Steckmeier et al., "Experiences with Rotation Atherectomy and Atherectomy", Herz, Feb. 1989, vol. 14, No. 1, pp. 43-51.

Di Sciascio et al., "Directional Coronary Atherectomy: From Therapeutic Device to Research Tool in Coronary Artery Disease", Cardiologla, Apr. 1999, vol. 44, No. 4, pp. 333-339.

Ikeno et al., "Early Experience With a Novel Plaque Excision System for the Treatment of Complex Coronary Lesions", Catheterization and Cardiovascular Interventions, 2004, vol. 61, pp 35-43.

Cook et al., "DNA Microarrays: Implications for Cadriovascular Medicine", Circulation Research, 2002, vol. 91, pp. 559-564.

Patino et al., "Serial Analysis of Gene Expression: Technical Considerations and Applications to Cardiovascular Biology", Circulation Research, 2002, vol. 91, pp. 565-569.

Levy et al., "Microarray Analysis of Neointima: Flowing Toward a Clear Future", Arterioscler Thromb Vasc Biol., 2002, vol. 22, pp. 1946-1947.

Ye et al., "Microarray, SAGE and their Applications to Cardiovascular Diseases", Cell Research, 2002, vol. 12, No. 2, pp. 105-115.

Gonschior et al., "Results of Directional Peripheral Atherectomy with Reference to Histology, Histochemistry, and Ultrastructure", The Journal of Vascular Diseases, Jun. 1993, pp. 454-463.

Johnson et al., "Primary Peripheral Arterial Stenoses and Restenoses Excised by Transluminal Atherectomy: A Histopathologic Study", J Am Coll Cardiol, Feb. 1990, vol. 15, No. 2, pp. 419-425.

Waller et al., "Histologic Analysis of Directional Coronary Atherectomy Samples: A Review of Findings and their Clinical Relevance", The American Journal of Cardiology, Oct. 18, 1993, vol. 72, pp. 80E-87E.

DiSciascio et al., "Histopathologic Correlates of Unstable Ischemic Syndromes in Patients Undergoing Directional Coronary Atherectomy: In Vivo Evidence of Thrombosis, Ulceration, and Inflammation", Am Heart J., Sep. 1994, vol. 128, No. 3, pp. 419-426.

Krings et al., "Ultrastructural and Proliferation Studies of Human, Catheter Atherectomy Extracted Plaque Material", Vasa Suppl., 1991, vol. 33, pp. 149-150.

Bauriedel et al., "Cellularity and Ultrastructural Characteristics of Human Atherectomy Specimens: Comparison Between Resenosis and Primary Stenotic of Coronary and Peripheral Lesions", Z Kardiol., Aug. 1993, vol. 82, No. 8, pp. 485-493.

Hofling et al., "Analysis of Atherectomy Specimens", Am J Cardiol, Oct. 18, 1983, vol. 72, No. 13, pp. 98E-107E.

MacLeod et al., "Proliferation and Extracellular Matrix Synthesis of Smooth Muscles Cultured From Human Coronary Atherosclerotic and Restenotic Lesions", J Am Coll Cardiol., Jan. 1994, vol. 23, No. 1, pp. 59-65.

Hanke et al., "Accumulation of Macrophages in the Arterial Vessel Wall Following Experimental Balloon Angioplasty", Eur Heart J, May 1994, vol. 15, No. 5, pp. 691-698.

Zohlnhöfer et al., "Gene Expression Profiling of Human Stent-Induced Neointima by cDNA Array Analysis of Microscopic Specimens Retrieved by Helix Cutter Atherectomy", Circulation, 2001, vol. 103, pp. 1396-1402.

Williams et al., "Directional Coronary Atherectomy: But Wait, There's More", Circulation, 1998, vol. 97, pp. 309-311.

Hofling et al., "Angiography and Functional Results and Histologic Findings Following Percutaneous Atherectomy in Patients with Arterial Occlusive Disease", Z Kardiol, Sep. 1989, vol. 78, No. 9, pp. 561-565.

Grant et al., "Expression of IGF-I, IGF-I Receptor and IGF Binding Proteins-1, -2, -3, -4 and -5 in Human Atherectomy Specimens", Regul Pept., Dec. 17, 1996, vol. 67, No. 3, pp. 137-144.

Taylor et al., "Proliferative Activity in Coronary Atherectomy Tissue, Clinical, Histopathologic, and Immunohistochemical Correlates", Chest, Sep. 1995, vol. 108, No. 3, pp. 815-820.

Yutani et al., "Histologic Evidence of Foreign Body Granulation Tissue and De Novo Lesions in Patients with Coronary Stent Restenosis", Cardiology, 1999, vol. 92, No. 3, pp. 171-177.

Veinot et al., "Preliminary Clinical Experience with the Pullback Atherectomy Catheter and the Study of Proliferation in Coronary Plaques", Can J Cardiol, Dec. 1998, vol. 14, No. 12, pp. 1457-1463.

Arbustini et al., "Histopathologic Features in Atherectomy Samples Obtained From Patient with Unstable Angina, Stable Angina and Restenosis, Direct Atherectomy Lombardi Group", G Ital Cardiol., Jun. 1996, vol. 26, No. 6, pp. 623-633.

Ellis et al., "Relation of Clinical Presentation, Stenosis Morphology, and Operation Technique to the Procedural Results of Rotational Atherectomy and Rotational Atherectomy-Facilitated Angioplasty", Circulation, Feb. 1994, vol. 89, No. 2, pp. 882-892.

Ellis et al., "Relation of Stenosis Morphology and Clinical Presentation to the Procedural Results of Directional Coronary Atherectomy", Circulation, Aug. 1991, vol. 84, No. 2, pp. 644-653.

Dartsch et al., "Cell Constitution and Characteristics of Human Atherosclerotic Plaque Selectively Removed by Percutaneous Atherectomy", Atherosclerosis, Dec. 1989, vol. 80, No. 2, pp. 149-157.

* cited by examiner

TESTING LUMENECTOMY SAMPLES FOR MARKERS OF NON-VASCULAR DISEASES

TECHNICAL FIELD OF THE INVENTION

This invention is related to the area of disease diagnosis and prognosis. In particular, it relates to testing for disease markers in lumenectomy samples, such as samples from a blood vessel.

BACKGROUND OF THE INVENTION

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

One conventional treatment for cardiovascular disease is the use of stents. Endoluminal stents are commonly used to treat obstructed or weakened body lumens, such as blood vessels and other vascular lumens. Once deployed in the blood vessel, the stent can remain in the body lumen where it will maintain the patency of the lumen and/or support the walls of the lumen which surround it. One factor impeding the success of stent technology in endoluminal treatments is the frequent occurrence of in-stent restenosis, characterized by proliferation and migration of smooth muscle cells within and/or adjacent to the implanted stent, causing reclosure or blockage of the body lumen.

Atherosclerosis and restenosis can be treated in a variety of ways, including drugs, bypass surgery, and a variety of catheter-based approaches which rely on intravascular debulking or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon to urge the aperture against the material to be removed.

Although atherectomy catheters have proven very successful in treating many types of atherosclerosis and in-stent restenosis, improved atherectomy catheters and methods are continuously being pursued. For example, many currently available side-cutting atherectomy catheters have difficulty in capturing occluding material in the cutting aperture. To facilitate material capture, the cutting aperture is frequently elongated to increase the area into which the material can penetrate. Such elongation typically requires an equivalent lengthening of the cutter housing. Since most cutter housings are rigid, such lengthening makes it more difficult to introduce the distal end of the catheter through tortuous regions of the vasculature.

Another shortcoming of many currently available atherectomy catheters is that they typically require a balloon positioned opposite the cutting window to urge the cutting window into contact with occluding material. Such balloons, however, unduly increase the size of the distal portion of the catheter. Even with the balloon, the amount of material that can be removed by conventional atherectomy catheters is limited by the size of the cutting window. Other disadvantages of some catheters include cutting elements with less than ideal hardness, inadequate storage space within the catheter for containing removed material, sub-optimal guide wire lumens, and/or the like. In addition, the available atherectomy catheters generally provide material insufficient in quantity and/or quality for testing by many histological, array, proteomic or other biochemical or molecular methods. For example, in one report a device and method available to the artisan collected less than about 50 mg of tissue. (Safian et al., Circulation 82: 305-307 (1990)). This amount of material is not typically enough to carry out more than one test, or is insufficient to successfully carry out a number of diagnostic tests available to the physician or researcher.

Recently atherectomy catheters have been developed which can access small, tortuous regions of the vasculature and remove atheromatous and other occluding materials from within blood vessels and stents in a controlled fashion. In particular, these atherectomy catheters facilitate capturing and invagination of atheromatous materials. Particularly, these catheters are capable of in vivo capturing and removing of continuous tissue strands of sufficient quantity and quality for testing in vitro. These catheters and methods for their use are adaptable for use in a variety of body lumens, including but not limited to coronary and other arteries.

There is a continuing need in the art to develop new methods for accurate and early assessments of disease states and incipient or imminent disease states.

SUMMARY OF THE INVENTION

One aspect of the invention provides a method of determining the presence or likelihood of a condition of a patient. A lumenectomy material comprising at least one continuous tissue strand collected in vivo from an inner surface of a body lumen of a subject is tested for the presence of at least one marker of a disease selected from the group consisting of hypertension, hyperlipidemia, depression, obesity, metabolic syndrome, insulin resistance, kidney damage, and diabetes. The patient is identified as having or as likely to develop the disease if a marker of the disease is identified in the lumenectomy material of the subject.

This and other embodiments which will be apparent to those of skill in the art upon reading the specification provide the art with methods for detection, diagnosis, and prognosis of diseases.

DETAILED DESCRIPTION OF THE INVENTION

The inventors have developed methods for testing for the presence or likelihood of certain diseases. Rather than testing for certain disease makers in serum, for example, the present methods test for disease markers in lumenectomy samples, such as artherectomy samples.

Diseases which can be evaluated using the method of the invention include, but are not limited to, hypertension, hyperlipidemia, depression, obesity, diabetes, insulin resistance, metabolic syndrome, kidney disease, and kidney damage. Lumens from which the test sample can be harvested include blood vessels, such as the coronary artery, the gastrointestinal tract, such as the intestine, airways, such as the bronchi and the trachea, tear ducts, mammary ducts, kidney tubules, ureters, bladders, urethras, vas deferens, epididymis, and fallopian tubes.

Lumenectomy catheters which can be used to collect the samples of the present invention are described in U.S. application publication No. 20050177068, the disclosure of which is expressly incorporated herein. Other lumenectomy catheters which provide sufficient material for testing may also be used. In certain embodiments the amount of material collected can be about 1 mg to about 2000 mg, more typically the amount of material can be about 1 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, or about 800 mg up to about 2000 mg.

The material excised from the body lumen will vary in length and will depend on the catheter configuration, the type of material removed, the body lumen, and the like. However, in certain embodiments, the material will be in the form of continuous strands that have a substantially consistent depth and width of tissue cuts. The material is typically longer than the length of the cutting window (but it may be shorter), and typically has a length of at least about 2.0 mm, although the length may be between about 0.5 cm up to about 10 cm or longer in length. Advantageously, the planing action of the catheter provides a material tissue structure that reflects the actual in vivo tissue structure, and provides information about larger portions of the disease state of the body lumen.

Markers which can be tested are any for which an association has been established between the marker and the disease or imminent onset of the disease. Markers can be, for example, proteins, enzymes, or RNAs. The marker can be the presence or absence of a substance or an increased or decreased level of the substance. The material collected from the body lumen is typically a continuous strip of tissue that may be longer than the cutting window of the lumenectomy catheter. This material can provide a sufficient amount of sample material of a quality and quantity that can be used for one or more of genomic screening, DNA hybridization, RNA hybridization, gene expression analysis, PCR amplification, proteomic testing, drug efficacy screening, protein marker detection, DNA marker detection, RNA marker detection, histological testing, histopathology, cytopathology, cell and tissue type analysis, biopsy, or the like. In addition, the material collected may be sufficient in amount and quality for testing for one or more of the presence of a DNA, an RNA, or a protein marker.

Generally the markers may be in the category of apoptotic markers, cell cycle proteins, transcriptional factors, proliferative markers, endothelial growth factors, adhesion molecules, cytokines, chemokines, chemokine receptors, inflammation markers, coagulation factors, fibrinolytic factors, oxidative stress related molecules, extracellular matrix molecules, interleukins, growth factors, glycoproteins, proteoglycans, cell-surface markers, serum markers, or immune factors. Other types of markers which are established as associated with the diseases may be used as well.

Specific markers which may be used include C-reactive protein, interleukin-6, and/or intracellular adhesion molecule-1 for depression; angiotensin II, aldosterone, and/or atrial natriuretic factor for hypertension; tissue factor pathway inhibitor, plasminogen activator inhibitor-1, triglycerides, and/or apolipoprotein B for hyperlipidemia; triglycerides for insulin resistance; low density lipoprotein, Remnant-like particles-cholesterol and/or triglycerides for diabetes; triglyceride-rich lipoproteins for kidney damage. Other markers as are known in the art and which are associated with specific diseases can be used as well, without limitation.

Particular types of tests that can be carried out successfully on the excised lumenectomy material removed by the methods of the present invention include, but are not limited to, enzyme histochemistry, immunohistology, immunocytochemistry, immunoassays, immunofluorescent assays, immunoprecipitation assays, ELISA, flow cytometry, fluorescent activated cell sorting, radioimmunochemistry, electrophoresis, two-dimensional gel electrophoresis, Western blotting, protein sequencing, mass spectrometry, proteomic analysis, and protein microarray analysis. Further, Nothern blotting, RNase protection assays, in situ hybridization assays, DNA microarray testing, reverse transcription polymerase chain reaction PCR (RT-PCR), Southern blotting, DNA sequencing, PCR amplification, single strand conformational polymorphism assays, single strand polymorphism (SNP) assays, and serial analysis of gene expression (SAGE) assays can be successfully carried out with the lumenectomy material compositions collected by the disclosed methods.

Prior to testing the harvested material, the material can optionally be placed in a preserving agent, a tissue fixative, or a preparation agent compatible with a particular test to be run. Agents known in the art for preserving, fixing or preparing the material for later use include, for example, saline, heparinized saline, liquid nitrogen, formalin, a membrane lysis agent, an RNA or DNA preparation agent, and the like. The material can be collected in a single access or can be collected in multiple translumenal accesses in the same patient. Further the material is typically at least one substantially consistent, continuous strip of material that maintains the structure of the material as it was removed from the inner surface of the lumen of the patient. Also, sample material can be collected from one, two, or more sites in the same or a different body lumen of a patient.

The lumenectomy catheters can achieve selective plaque excision, i.e., they can specifically target diseased areas. Thus the samples are enriched in disease markers, relative to serum samples, in which disease markers are diluted with other substances from non-diseased tissues. Nonetheless, serum testing may be performed in conjunction with the lumenectomy evaluation, and the results used, for example, to confirm each other.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

REFERENCES

The disclosure of each reference cited is expressly incorporated herein.
Yu H. et al., *Hypertension* 2000; 35:135
Raij, L., *Hypertension*, 2001; 37:767
Tomiyama, H., et al., *Hypertension*, 2005; 45:997
Guo, X., et al., *Hypertension*, 2005; 45:799
Sarnak, M. et al., *Hypertension*, 2003; 42:1050
Cassidy, A., et al., *Circulation*, 2005; 111:1877-1882
Empana, J. P., et al., *Circulation*, 2005; 111:2299-2305
Bolterman, R. et al., *Hypertension*, 2005, doi: 10/1161/01.HYP.0000174602.59935.D5
Preston, R., et al., *Hypertension*, 2003; 41:211
Zitoun, D., et al., *Arteriosclerosis, Thrombosis, and Vascular Biology*. 1996; 16:77-81

Sijbrands, E., et al., *Arteriosclerosis, Thrombosis, and Vascular Biology.* 1999; 19:2722

Mar, R., et al., *Circulation Research.* 2004; 94:993

Twickler, T. B., et al., *Circulation.* 2004; 109:1918-1925

We claim:

1. A method for diagnosing a disease in a patient, the method comprising:
    a) employing a catheter so as to collect lumenectomy material from an inner surface of a lumen of a body of said patient in a manner sufficient to ensure that the structure of the collected lumenectomy material retains the actual in vivo tissue structure, wherein the catheter is employed in such a manner that it planes across the inner surface of the body lumen and said planing action of the catheter results in the collection of the lumenectomy material; and further wherein the lumenectomy material comprises one continuous strand having:
        a substantially consistent depth and width,
        a length that ranges from about 2.0 mm to about 10 cm, and
        a mass that ranges from 1 mg to about 2000 mg;
    b) performing a test on said lumenectomy material to obtain test results, wherein the lumenectomy material retains the actual in vivo tissue structure throughout the test and wherein said test results in the identification of at least one marker of a disease selected from the group consisting of hypertension, hyperlipidemia, depression, obesity, metabolic syndrome, insulin resistance, kidney damage, and diabetes; and
    c) diagnosing said patient for said disease based on said test results, wherein the disease is selected from the group consisting of hypertension, hyperlipidemia, depression, obesity, metabolic syndrome, insulin resistance, kidney damage, and diabetes.

2. The method according to claim 1, wherein the test further results in the identification of an increased or decreased level of the marker as compared with a non-disease condition.

3. The method according to claim 1, wherein said catheter comprises a housing and said housing comprises an aperture for collecting said lumenectomy material.

4. The method according to claim 3, wherein the catheter further comprises a blade.

5. The method according to claim 4, wherein the blade is translated via the aperture.

6. The method according to claim 5, wherein said aperture is elongated and further comprises a cutting window.

7. The method according to claim 6, wherein the lumenectomy material comprises a length that is longer than a length of the cutting window.

8. The method according to claim 7, wherein the lumenectomy material is collected by translating the blade outside of the cutting window of the aperture.

9. The method according to claim 8, wherein the blade and cutting window are advanced together so as to obtain the collection of the lumenectomy material.

10. The method according to claim 3, wherein the planing action of the catheter results in the collection of said lumenectomy material within the aperture.

11. The method according to claim 5, wherein translation of the blade results in the collection of the lumenectomy material.

12. The method according to claim 1, wherein the length of the material ranges from about 2.0 mm to about 0.5 cm.

13. The method according to claim 1, wherein the markers comprises one or more of a member selected from the group consisting of a DNA, a protein, and a RNA.

14. The method according to claim 1, wherein the test further results in the identification of the presence or absence of the marker.

15. The method according to claim 1, further comprising the collection of the lumenectomy material from a plurality of sites within said lumen of the patient's body.

16. The method according to claim 1, further comprising the collection of the lumenectomy material from a plurality of lumens within the patient's body.

17. The method according to claim 1, wherein the lumen comprises a diseased tissue.

18. The method according to claim 17, wherein the diseased tissue comprises a plaque.

19. The method according to claim 18, further comprising testing the patient's serum for the diseased marker.

20. The method according to claim 19, wherein the plaque is enriched in disease markers in comparison to the patient's serum.

21. The method according to claim 1, wherein the at least one marker of disease is a member selected from the group consisting of C-reactive protein, interleukin-6, intracellular adhesion molecule-1, angiotensin, vascular adhesion molecule-1, monocyte chemoattractant protein-1, aldosterone, atrial natriuretic factor, tissue factor pathway inhibitor, plasminogen activator inhibitor-1, triglycerides, apolipoprotein B, low density lipoprotein (LDL) particles, Remnant-like particles-cholesterol (RLP-C), and triglyceride-rich lipoproteins (TRL).

22. The method according to claim 1, wherein said test comprises one or more of a member selected from the group consisting of genomic screening, DNA hybridization, RNA hybridization, gene expression analysis, PCR amplification, proteomic testing, drug efficacy screening, protein marker detection, DNA marker detection, RNA marker detection, histological testing, histopathology, cytopathology, cell and tissue type analysis, and a biopsy.

23. The method according to claim 1, wherein the test comprises one or more of a member selected from the group consisting of enzyme histochemistry, immunohistology, immunocytochemistry, an immunoassay, an immunofluorescent assay, an immunoprecipitation assay, ELISA, flow cytometry, fluorescent activated cell sorting, radioimmunochemistry, electrophoresis, two-dimensional gel electrophoresis, a Western blot, protein sequencing, mass spectrometry, proteomic analysis, protein microarray analysis, a Nothern blot, an RNase protection assay, an in situ hybridization assay, DNA microarray testing, reverse transcription polymerase chain reaction PCR (RT-PCR), a Southern blot, DNA sequencing, PCR amplification, a single strand conformational polymorphism assay, a single strand polymorphism (SNP) assay, and a serial analysis of gene expression (SAGE) assay.

24. The method according to claim 1, wherein said marker comprises one or more of a member selected from the group consisting of apoptotic markers, cell cycle proteins, transcriptional factors, proliferative markers, endothelial growth factors, adhesion molecules, cytokines, chemokines, chemokine receptors, inflammation markers, coagulation factors, fibrinolytic factors, oxidative stress related molecules, extracellular matrix molecules, interleukins, growth factors, glycoproteins, proteoglycans, cell-surface markers, serum markers, and immune factors.

25. The method according to claim 1, wherein the markers comprises one or more of a member selected from the group consisting of C-reactive protein, interleukin-6, intracellular adhesion molecule-1, angiotensin II, aldosterone, atrial natriuretic factor, tissue factor pathway inhibitor, plasminogen activator inhibitor-1, triglycerides, apolipoprotein B, low density lipoprotein, Remnant-like particles, cholesterol, and triglyceride-rich lipoproteins.

* * * * *